United States Patent [19]
Fontaine

[11] Patent Number: 5,443,498
[45] Date of Patent: Aug. 22, 1995

[54] VASCULAR STENT AND METHOD OF MAKING AND IMPLANTING A VACSULAR STENT

[75] Inventor: Arthur B. Fontaine, Fresno, Calif.

[73] Assignee: Cook Incorporated, Bloomington, Ind.

[21] Appl. No.: 162,825

[22] Filed: Dec. 6, 1993

Related U.S. Application Data

[63] Continuation of Ser. No. 874,347, Apr. 24, 1992, abandoned, which is a continuation-in-part of Ser. No. 858,304, Mar. 25, 1992, abandoned, which is a continuation-in-part of Ser. No. 769,216, Oct. 19, 1991, Pat. No. 5,314,472.

[51] Int. Cl.⁶ .......................... A61F 2/06; A61M 29/02
[52] U.S. Cl. .......................................... 623/1; 623/12; 606/195
[58] Field of Search .................. 623/1, 11, 12; 600/36, 600/194, 195

[56] References Cited

U.S. PATENT DOCUMENTS

| | | |
|---|---|---|
| 4,512,338 | 4/1985 | Balko et al. ................. 128/1 R |
| 4,553,545 | 11/1985 | Maass et al. . |
| 4,580,568 | 4/1986 | Gianturco ................... 128/345 |
| 4,649,922 | 3/1987 | Wiktor ...................... 128/344 |
| 4,655,771 | 4/1987 | Wallsten . |
| 4,665,918 | 5/1987 | Garza et al. ................ 128/343 |
| 4,733,665 | 3/1988 | Palmaz . |
| 4,739,762 | 4/1988 | Palmaz . |
| 4,776,337 | 10/1988 | Palmaz ....................... 623/1 |
| 4,787,899 | 11/1988 | Lazarus . |
| 4,795,458 | 1/1989 | Regan . |
| 4,800,882 | 1/1989 | Gianturco ................... 128/343 |
| 4,820,298 | 4/1989 | Leveen et al. ............... 623/1 |
| 4,830,003 | 5/1989 | Wolff et al. . |
| 4,856,516 | 8/1989 | Hillstead . |
| 4,878,906 | 11/1989 | Lindemann et al. . |
| 4,886,062 | 12/1989 | Wiktor . |
| 4,893,623 | 12/1989 | Rosenbluth . |
| 4,922,905 | 5/1990 | Strecker . |
| 4,950,227 | 8/1991 | Savin et al. ................. 623/10 |
| 4,954,126 | 9/1990 | Wallsten . |
| 4,969,458 | 11/1990 | Wiktor ...................... 606/194 |
| 4,969,890 | 11/1990 | Sugita et al. . |
| 5,015,253 | 5/1991 | MacGregor .................. 623/1 |
| 5,019,090 | 5/1991 | Pinchuk ...................... 606/194 |
| 5,035,706 | 7/1991 | Gianturco ................... 606/198 |
| 5,041,126 | 8/1991 | Gianturco ................... 606/195 |
| 5,133,732 | 7/1992 | Wiktor ...................... 606/195 |
| 5,135,536 | 8/1992 | Hillstead ................... 623/1 |
| 5,197,978 | 3/1993 | Hess ......................... 623/1 |
| 5,217,483 | 6/1993 | Tower ........................ 673/1 |
| 5,224,953 | 6/1993 | Morgentaler ................. 623/12 |

FOREIGN PATENT DOCUMENTS 183372 2/1986 European Pat. Off. .... A61M 29/00

*Primary Examiner*—David Isabella
*Assistant Examiner*—Debra S. Brittingham
*Attorney, Agent, or Firm*—Richard J. Godlewski

[57] ABSTRACT

A vascular stent includes a continuous wire which is formed into a substantially tubular body having a plurality of oblong, open cells which are staggered around the circumference of the tube. When the body is formed in its unexpanded state, the long sides of each oblong cell are arranged substantially parallel to the longitudinal axis of the tubular body. Adjoining cells may then be bonded together at a point between adjacent parallel sides on a cell. When the body is expanded, the adjacent sides of each cell extend oblique to the longitudinal axis of the body.

21 Claims, 6 Drawing Sheets

VASCULAR STENT AND METHOD OF MAKING AND IMPLANTING A VACSULAR STENT

Related Application:

This application a continuation of utility patent application No. 07/874,347, filed Apr. 24, 1992, now abandoned, which is a continuation-in-part of copending utility patent application Ser. No. 07/858,304, filed Mar. 25, 1992, now abandoned, for Vascular Stent, which is commonly assigned herewith and the disclosure of which is incorporated herein it its entirety, which in turn is a continuation-in-part of copending utility patent application Ser. No. 07/769,216, filed Oct. 1, 1991, now U.S. Pat. No. 5,314,472 for Vascular Stent, which is commonly assigned herewith and the disclosure of which is incorporated herein in its entirety, which in turn is a continuation of copending design patent application Ser. No. 07/723,525, filed Jun. 28, 1991, for Vascular Stent. Copending utility patent application Ser. No. 07/858,304 is also a continuation of copending design patent application Ser. No. 07/847,247, filed Mar. 9, 1992, for Stent, which in turn is a continuation-in-part of copending design patent application No. 07/723,525, filed Jun. 28, 1991, for Vascular Stent.

BACKGROUND OF THE INVENTION

The present invention relates to medical devices and, more particularly, to vascular stents.

Stents are prosthetic devices which are implanted inside a lumen in order to provide support for and assure patency of the lumen. Patency is particularly important in the field of angioplasty which is concerned with the repair and reconstruction of blood vessels. Stents are frequently implanted within the vascular system to reinforce collapsing, partially occluded, weakened, or abnormally dilated sections of blood vessels. More generally, however, stents can also be used inside the lumen of any physiological conduit including the arteries, veins, bile ducts, urinary tract, alimentary tract, tracheobronchial tree, cerebral aqueduct, and genitourinary system. Stents can also be used inside lumina of animals besides humans.

One common procedure for implanting a stent in a blood vessel involves mounting the stent on a catheter. The catheter is then slipped through an incision in the vessel wall and down the length of the vessel until it is positioned to bridge a diseased or narrowed portion of the vessel. If the stent is expandable, it may be mounted on a balloon-tip catheter in its unexpanded form and then expanded in place against the inside wall of the vessel at the same time as the vessel is being dilated by the balloon.

Conventional stent designs have been found to have many shortcomings. For example, U.S. Pat. No. 4,553,545 to Maass et al. discloses a device for application in blood vessels including a helically shaped coil spring that can be expanded from a first state of a certain diameter to a second state of a larger diameter (and vice versa) by rotating the ends of the coil relative to each other. The length of the spring may be maintained during the transition from the first state to the second state by changing the number of spring turns and the corresponding pitch of the spring as the coil is wound. When the Maass design is applied to surgical operations in the human body, the expansion degree is limited to about fifty percent for an expansion number of 1.5.

The large size and limited expendability of the Maass design necessitates a relatively large incision in the vessel wall before it can be inserted with a catheter. The Maass device may, therefore cause excessive vessel damage and bleeding during implantation, especially when it is used inside large vessels such as arteries. Furthermore, changing the number of turns and pitch of the Maass coil a vessel may damage the vessel intima as the outside edges of each coil, and the ends of the stent, rub against the interior wall of the vessel. Moreover, unless the ends of the Maass device are translationally fixed during expansion of the coil, the ends of the coil may migrate along the axis of the stent and cause further damage to the inside of the lumen. Consequently, the Maass design is difficult to expand once it is in place inside the lumen.

Cesare Gianturco and Gary Roubin have developed the so-called "Gianturco-Roubin" stent illustrated in FIG. 1. This stent is constructed of monofilament stainless steel alloy wire 0.006 inches in diameter which is configured in the shape of an incomplete coil. The stent is balloon expandable and may be premounted on a polyethylene balloon catheter. The two-to-one expansion ratio of this stent limits this design to small vessel applications. Large vessels such as aorta would require a prohibitively large introduction system and therefore put the vessel at risk for excessive bleeding.

The present inventor has found that vascular stents require substantial flexibility in their unexpanded state in order to allow them to bend and conform to the tortuous shape of the vessels through which they are inserted. This need for flexibility during insertion is especially important for older patients since their blood vessels tend to be more tortuous and less flexible than those of younger patients. The present inventor has also found that, vascular stents should be rigid and have a high hoop strength in their expanded state. Although the reasons for the success of rigid stents are not entirely clear, it has been suggested that rigid stents are less likely to pulsate inside vessels, and therefore, they are less likely to rub against the vessel intima once they are in place. The Gianturco-Roubin stent suffers from the limitation that it is not particularly rigid in its expanded state. The openness of the one side of the Gianturco-Roubin coil design also results in an irregular lumenal appearance that may predispose the ingrowth of tissue through the coils. Overexpanding the stent may increase the size of this open portion and thus increase the possibility for excessive tissue ingrowth.

Gianturco has also disclosed the self-expanding "Z" stent illustrated in FIG. 2. This device has been found generally unsuitable for small vessel cardiovascular applications because it does not perform well in medium or low flow situations. Sizes below five millimeters have been found to be very difficult to make and securely implant inside patients. Furthermore, the Gianturco "Z" stent can only be expanded to one size which depends on the constrictive force applied against it by the vessel wall.

U.S. Pat. No. 4,922,905 to Strecker discloses a dilation catheter using a tube-like knitted structure. Before expansion, the individual meshes interlock loosely in a looped pattern. During radial expansion, the loops are deformed beyond the elastic limit of the filament material. In practice, it has been found that such woven stents use excessive material which may disturb the flow of blood through the stent and cause excessive tissue formation and thrombosis on the inside of the vessel. Furthermore, the woven design creates a highly flexible stent with limited loop strength which is undesireable for the reasons previously noted above.

U.S. Pat. Nos. 4,733,655, 4,739,762, and 4,776,337 to Palmaz discloses an expandable intraluminal graft. FIGS. 1A and 1B of Palmaz '665 illustrate a prosthesis made from diagonal elongate members which are stainless steel wires having a cylindrical cross section. The elongate members are preferably fixed to one another where they intersect in order to provide a relatively high resistance to radial collapse. The prosthesis is preferably made of continuous wire woven in a crisscrossed tubular pattern to form a wire mesh tube. This configuration, however, creates tines or points at each end of the criss-crossed pattern where the ends of the elongate members intersect. These tines can easily cause damage to the catheter balloon or inside wall of the vessel. Furthermore, the length of the tube will decrease as it is externally expanded which can cause further damage to the internal lining of the vessel.

FIGS. 1A and 1B of Palmaz '762 illustrate a thin-walled tubular member having a plurality of slots disposed substantially parallel to the longitudinal axis of the tubular member. The slots are uniformly and circumferentially spaced by connecting members. After expansion, the slots assume a substantially hexagonal configuration. The width of the slots may be substantially reduced so that the expanded slots assume the configuration of a parallelogram.

The Palmaz '762 design also has several drawbacks. First, the axial length of graft will shorten as it expands. Second, the slots create weak points near the connecting members which can break during expansion. Third, the design has been found to have limited expansion of about 4–6 times its unexpanded diameter and a metal surface area of about 10% of its expanded state. Finally, for small unexpanded diameters it can be difficult to form the slots in the tube. Consequently, the Palmaz '762 design offers limited capabilities for both large and small diameter vessels.

It has been found by the present inventor that an ideal vascular prosthesis should include several features. The stent should be formed from as little material as possible with a low profile (i.e. diameter) in its unexpanded state so that it can be inserted through the smallest possible hole in the vessel wall in order to control bleeding and damage to the vessel. A low profile also allows the stent to be more easily moved through narrow vessels. Furthermore, it is preferable that the unexpanded profile of the stent be independent of its expansion ratio. In other words, besides needing the smallest possible profile during insertion, there is also a need to be able to change the ultimate expansion ratio of the stent without affecting its unexpanded profile so that one size stent can be used with almost any size lumen.

The stent should also have high flexibility in its unexpanded state and excellent hoop strength in its expanded state. In practice, it has been found to be difficult to design a stent with both of these characteristics. Flexibility is needed to insert the stent through tortuous lumens while hoop strength is needed to resist the radial forces from the artery once the stent is in place. The stent should also be rigid once it is expanded inside a vessel in order to minimize its movement against the vessel intima after it is in place and to promote healing of the vessel after placement. Furthermore, the flexibility of the design should be adjustable without changing the size or configuration of the stent.

The stent should be atraumatic to vessels and blood cells. It should therefore be formed from as little biocompatible material as possible. The stent should not have any exterior tines or sharp edges which could damage the wall of the vessel. It should also not have any interior tines which could damage the catheter balloon or cause hemodynamic disturbances which might interfere with the flow of blood through the stent. The material from which the stent is formed is preferably a low memory, radio-opaque material. In other words, the stent should maintain its shape without recoil once it is expanded inside the vessel and should be visible during fluoroscopy in order to be able to verify that the stent has not migrated from its intended position.

SUMMARY OF THE INVENTION

In a preferred embodiment, the vascular stent includes a continuous wire which is formed into a substantially tubular body. The wire forms a plurality of oblong, open cells which are staggered around the circumference of the tube. When the body is formed in its unexpanded state, the long sides of each oblong cell are arranged substantially parallel to the longitudinal or axis of the tubular body. Adjoining cells may then be bonded together at a point between adjacent parallel sides on a cell. When the body is expanded, the adjacent sides of each cell extend oblique to the longitudinal axis of the body.

BRIEF DESCRIPTION OF THE DRAWINGS

The invention will now be further described with reference to the following figures wherein like elements are provided with the same reference numerals.

DESCRIPTION OF THE PREFERRED EMBODIMENTS

Figure 1:
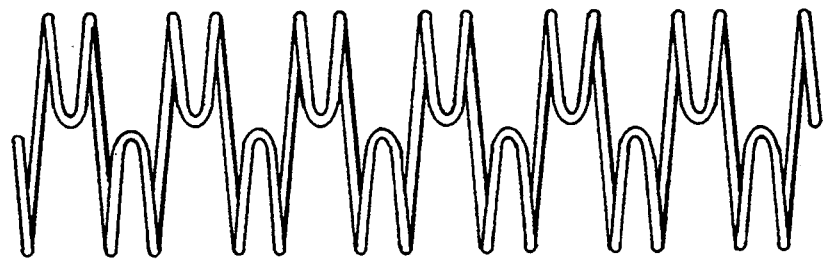
FIG. 1 is a side view of the Gianturco-Roubin stent which is known in the prior art.
Figure 2:
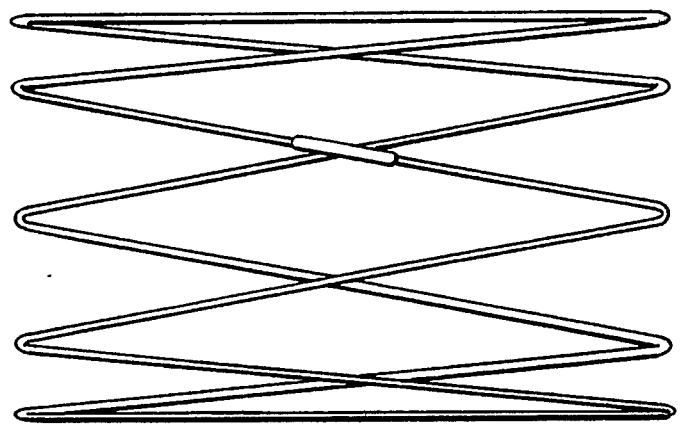
FIG. 2 is a side view of the Gianturco self-expanding "Z" stent which is also known in the art.
Figure 3:
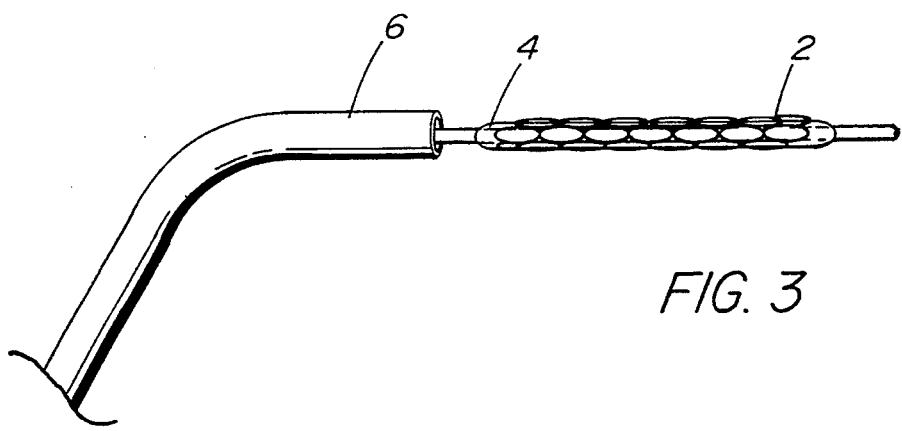
FIG. 3 is a side elevational view a preferred embodiment of the stent of the present invention in an unexpanded state arranged on an uninflated balloon catheter.
Figure 4:
FIG. 4 is a side elevational view of the stent of FIG. 3 removed from the catheter of FIG. 3.

FIG. 3 shows unexpanded stent 2 mounted on a catheter ready for insertion into a lumen. As shown in FIG. 4, unexpanded stent 2 has a tubular body which allows it to be slipped over catheter balloon 4. In a preferred method of implantation, the unexpanded stent 2 and catheter balloon 4 are withdrawn inside the sheath 6 while the sheath is slid inside a lumen such as a blood vessel. Once the unexpanded stent 2 is moved to its appropriate position, the sheath is partially withdrawn so that the unexpanded stent 2 and balloon 4 are exposed inside the lumen. The balloon 4 is then inflated and the stent 2 is expanded in place inside the lumen to assume the expanded form 8 illustrated in FIG. 5. The balloon 4 is then deflated and the catheter is removed from the lumen without the stent.

The stent is preferably formed from a continuous wire. The term "wire," as used here, should not be construed as limited to just metallic materials. In fact, the stent may be formed from any type of filament. The stent may also be made from groups of filaments or fibers which are wound or braided together in order to form a continuous filament. Also, several distinct filaments may also be attached together by any conventional means such as butt-welding. It is also possible to mold the stent in its unexpanded state.

To prevent the stent from recoiling to its unexpanded state after it has been implanted, the stent is preferably made from a "low memory" material that does not try to resume its original shape after its is deformed. Alternatively, the size of the wire can be chosen so that when the stent is expanded, the wire is stressed beyond its plastic yield point but not beyond the ultimate stress at which the material cracks or breaks. Both the unformed wire and the unexpanded stent may be annealed in order to reduce the stresses which are created in the wire during the stent formation process.

The stent material is preferably radio-opaque so that the location of the stent can be verified through fluoroscopic examination. The stent should also be made from a biocompatible (e.g., stainless steel) and/or bioabsorbable (e.g. Vicryl) material with a smooth surface for minimizing the stent's effect on surrounding tissue and bodily fluids such as blood. The stent may also be coated with antithromblytic or anticoagulatory agents such as Dextran, Heperin, t-PA, polytetrafluoroethylene, or ultra low-temperature isotropic carbon.

In a presently preferred embodiment, the stent is formed from about 0.006 to 0.020 inch diameter annealed tantalum wire.

Figure 6:
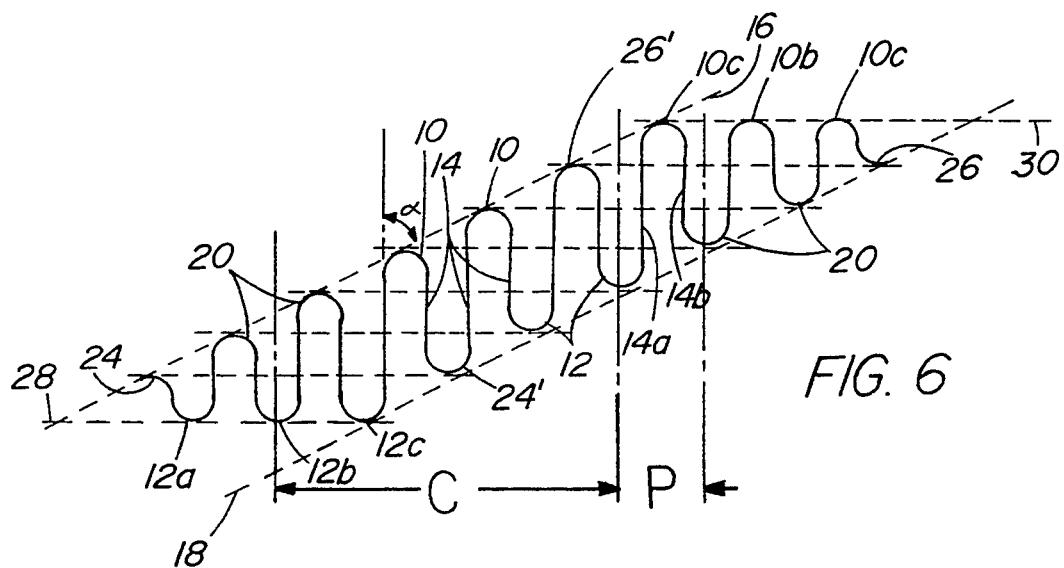
FIG. 6 is a schematic illustration of a planar waveform which is used to form the stent of FIG. 4.

The stent is formed from a continuous wire shaped into the planar pattern or waveform illustrated in FIG. 6. The pattern in FIG. 6 includes a series of alternating U-shaped waves having a period p with peaks 10 and valleys 12 interconnected by substantially straight sections 14. The straight sections 14 are substantially parallel to each other in FIGS. 6, 7, and 9 and are therefore depicted as straight vertical lines in those figures. However, the term "substantially parallel" also refers to the configuration of the straight portions 14 illustrated in the compressed planar (and generally sinusoidal) waveforms of FIGS. 8 and 10. The peaks 10 and valleys 12 are preferably semicircular and arranged to intersect straight portions 14 at the tangent of each curved peak or valley so that there are no discontinuities in the wire. However, other curved or linear shapes may also be used to form the peaks 10 and valleys 12. Each U-shape wave includes an ascending side 14a and a descending side 14b.

The outermost portions of the peaks 10 and valleys 12 in the middle section of the waveform are aligned along parallel axes 16 and 18, respectively. The axes 16 and 18 form an acute angle α with respect to the straight portions 14. The angle α is preferably 45 degrees so that if distance between each straight section is one unit, then each U-shaped wave in the middle section has one leg that is three units long while the other leg is four units long as illustrated by the parallel horizontal reference lines in FIG. 6. Other relative dimensions and angles, however, can be used. A curved stent can also be formed by, for example, slightly increasing the length of every third wave and decreasing the length of a corresponding wave in order to form an arched configuration where one side of the tubular body is slightly longer than another side.

There are two waves 20 of different amplitudes at each end of the stent which each have two sides of the same length. The end sections of the waveform include peaks 10a, 10b, and 10c at one end of the stent and valleys 12a, 12b, and 12c at the other end. The outer edges, or apexes, of valleys 12a, 12b, and 12c are aligned along axis 28 which is substantially perpendicular to the straight portions 14 (i.e., horizontal in FIG. 6). Similarly, the apexes of peaks 10a, 10b, 10c are aligned with an axis 30 which is also perpendicular to the straight portions 14 of the waves 22 but displaced from axis 30. The ends of the wire 24, 26 are preferably formed into half of a valley 12 at one end and half of a peak 10 at the other end. The ends 26 may also include a small, straight portion (not shown) which may be parallel or perpendicular to the straight portions 14.

Figure 7:
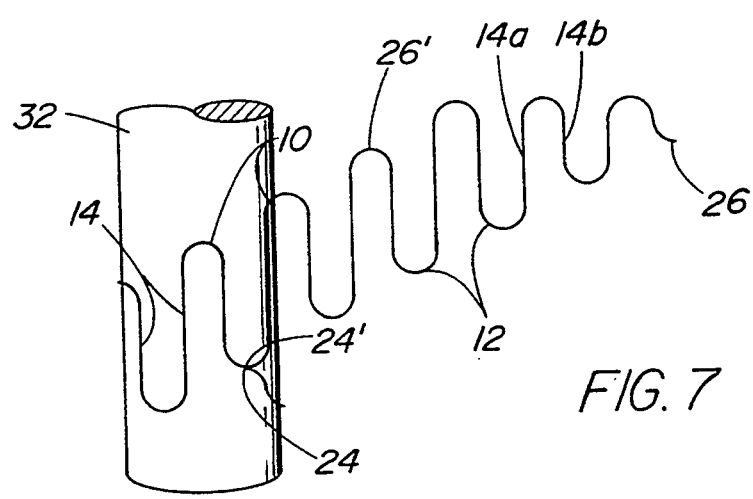
FIG. 7 illustrates the waveform of FIG. 6 being wrapped around a mandril.
Figure 8:
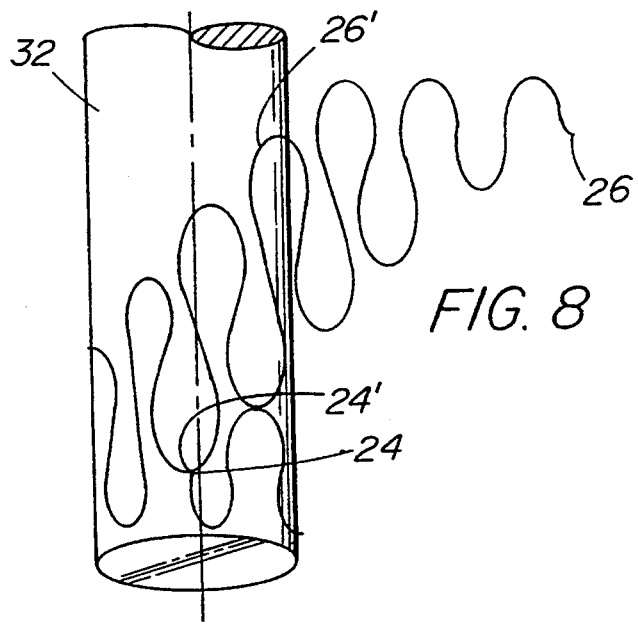
FIG. 8 illustrates an alternative embodiment of the waveform of FIG. 6 being wrapped around a mandril.

Referring to FIG. 7, the stent is formed by wrapping the waveform of FIG. 6 around a mandril 32. The circumference of the mandril 32 corresponds to the dimension c in FIG. 6 so that the peak 10 of one wave coincides with the valley 12 of another wave when the waveform of FIG. 6 is wrapped around mandril 32 with straight portions 14 aligned with the longitudinal, or central, axis of the mandril 32. FIG. 7 illustrates the end 24 of the waveform wrapped around the mandril 32 so that the end 24 is tangent to point 24'. Similarly, end 26 will be tangent to point 26' when the wave is completely wrapped around the mandril 32. The ends 24, 26 are then bonded by welding, brazing, soldering, tyeing, looping, adhesive bonding, or other suitable means to the points 24' and 26' respectively, so that the ends of the wire are not exposed where they could snag or otherwise interfere with the placement of the stent in the vessel.

In practice, electric resistance welding has been found to offer the most secure metal to metal bond by minimizing the amount of oxidation that occurs during bonding process. As the wire is wrapped on the mandril, some or all of the successive junctions between the peaks 10 and valleys 12 may be bonded in a similar manner until the stent is complete. The flexibility of the stent can be controlled by bonding fewer than all of the peaks 10 to corresponding valleys 11.

The stent may then be compressed on consecutively smaller diameter mandrils so that the straight sections 14 in FIG. 6 are no longer exactly parallel, but still substantially parallel, to the longitudinal axis of the mandril so the wave pattern takes on a generally sinusoidal shape such as the one illustrated in FIGS. 3, 4, 8 and 10. The planar waveform of FIG. 6 may also be compressed perpendicular to straight sections 14 in order to form the nearly sinusoidal pattern illustrated in FIG. 8 before being wrapped around the mandril 32. The stent is then removed from the smallest mandril and the stent is arranged on the balloon catheter, as shown in FIG. 3.

The structure of the stent of the present invention is capable of expanding radially when subjected to the internal pressure of an expanding catheter balloon. The peaks 10 and valleys 12 between the waves operate like flexible junctions or hinges to allow the straight portions 14 to swing outwardly, oblique to the central axis of the body of the stent. Unlike hinges, however, after the stent is expanded, the junctions resist displacement of the straight sections in the opposite direction (for example, due to the compressive force of the lumen) which would tend to reduce the diameter of the expanded stent. The resistance of these junctions to compression (i.e., hoop strength) is caused by placing a stress on the material at the junction which exceeds the elastic limit of the material, so that the material near the junction is plastically deformed and thus resists any tendency for the stent to collapse inside a lumen. The wire and the bonding material should therefore be a low memory material.

Figure 5:
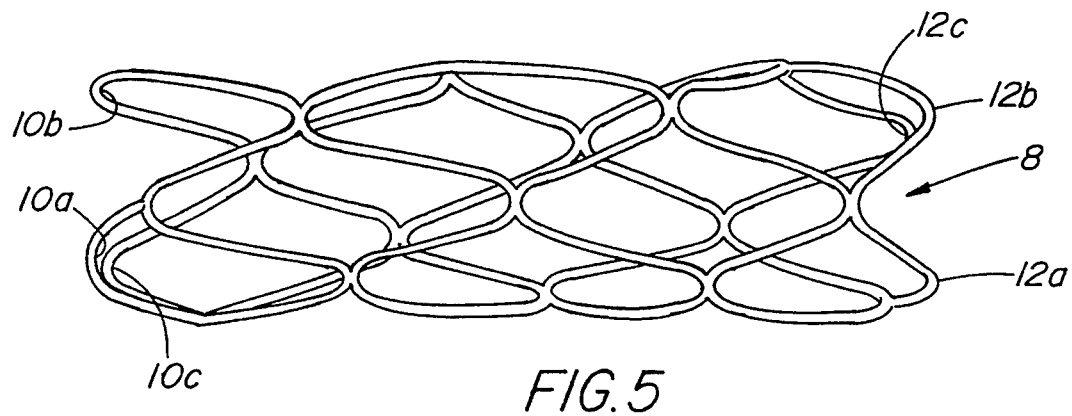
FIG. 5 is a side elevational view of the stent in an expanded state.

FIGS. 6 and 7 illustrate a waveform where the period (or wavelength) of each wave p is roughly one-fourth of the mandril circumference c. This configuration has been found to minimize the number of waves, the number of bonds between waves, and amount of wire required to adequately support the lumen. For the embodiments illustrated in FIGS. 6 and 7, the end of the stent will have three peaks 10a, 10b, and 10c, and three valleys 12a, 12b, and 12c exposed on the end of the expanded stent as illustrated in FIG. 5. The apex of peaks 10a, 10b, and 10c and valleys 12a, 12b, and 12c are equally spaced at 120, 240, and 360 degrees, respectively, around the end face of the stent. This preferred configuration provides the maximum lumen support and minimum profile (i.e. diameter) in the unexpanded state using the least possible amount of foreign material inside the body. Conventional stents have been found to use more than three peaks or valleys around the end circumference of the body which increases their unexpanded profile and uses more material than is necessary. When the stent is properly expanded, each apex of peaks 10a–10c and valleys 12a–12c moves only in the radial direction away from the longitudinal axis of the tubular body of the stent. Consequently, the present stent will not migrate inside a lumen during expansion.

Figure 10:
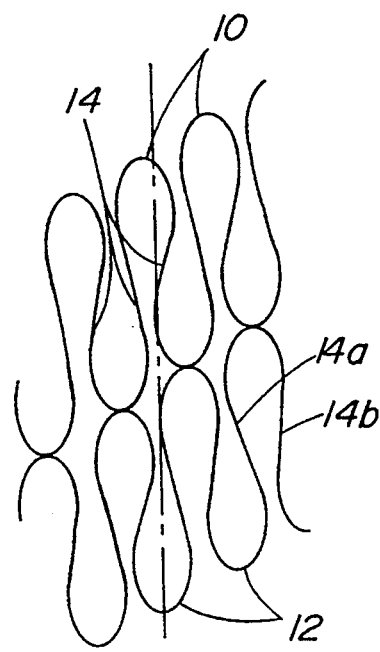
FIG. 10 shows the arrangement of the waves around the circumference of the mandril when the stent is formed in its unexpanded state as in FIG. 8.
Figure 9:
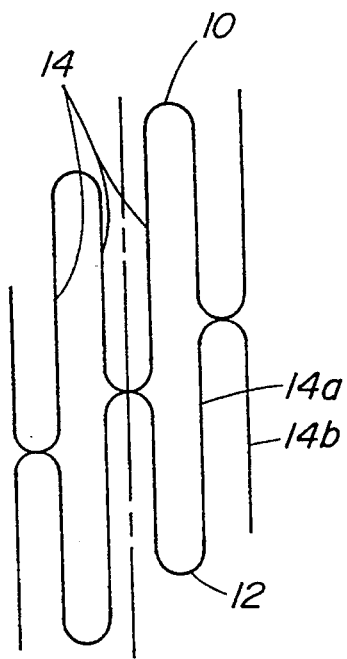
FIG. 9 shows the arrangement of the waves around the circumference of the mandril when the stent is formed in its unexpanded state as in FIG. 7.

FIGS. 9 and 10 illustrate the arrangement of the waves (from the waveforms of FIGS. 7 and 8, respectively) around the circumference of the mandril 32 or body of the stent when the stent is in its unexpanded state. In both FIGS. 9 and 10, the straight portions 14 are "substantially parallel" to longitudinal axis of the tubular body of the stent which is illustrated by the centerline in each of the Figures.

Figure 11:
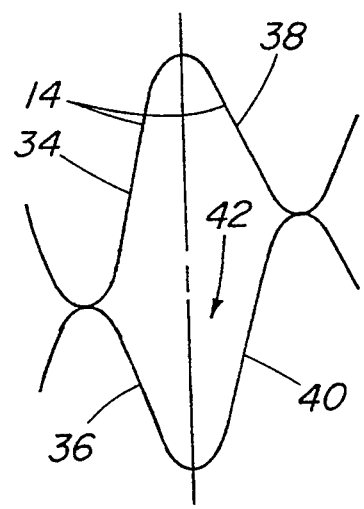
FIG. 11 is an enlargement of one of the cells in the stent of FIGS. 9 and 10 when the stent is in an expanded state.

FIG. 11 shows an enlargement of one of the cells 42 formed from the wave pattern of FIGS. 9 or 10 when the stent is in an expanded state. The cell 42 can also be described as a rhombic shape having four sides 34, 36, 38, and 40 where sides 34 and 36 are formed from one straight portion 14 and sides 38 and 40 are formed from another straight portion 14 which is adjacent to the other straight portion. The wire is preferably bonded at the point of tangency between adjacent sides 34, 36 and 38, 40 of cell 42. It is clear from FIG. 5 and FIG. 11 that straight portions 14 will extend oblique to the central axis of the tubular body (shown by the centerline in the figures) when the stent is expanded to form a rhombic shaped cell 42.

The ultimate degree of expansion or expansion ratio of the stent can be adjusted by changing the height of the waves defined by the distance between axis 18 and axis 20. Increasing the length of straight sections 14 increases the ultimate expansion ratio of the stent without affecting its unexpanded diameter or profile. Consequently, the ultimate expanded diameter of the stent is independent of its unexpanded diameter so that one size stent can be used with almost any size lumen. Moreover, even large lumens can be supported with a stent that has a small unexpanded profile so that bleeding and vessel damage is minimized during implantation. In practice, the stent has been found to work well with expansion ratios of between 1:1 and 10:1; however, larger expansion ratios are also possible. The ultimate expansion ratio can also be increased by decreasing the period of the waves p and/or the distance between straight sections 14 so that more waves are created around the circumference of the stent.

Figure 12:
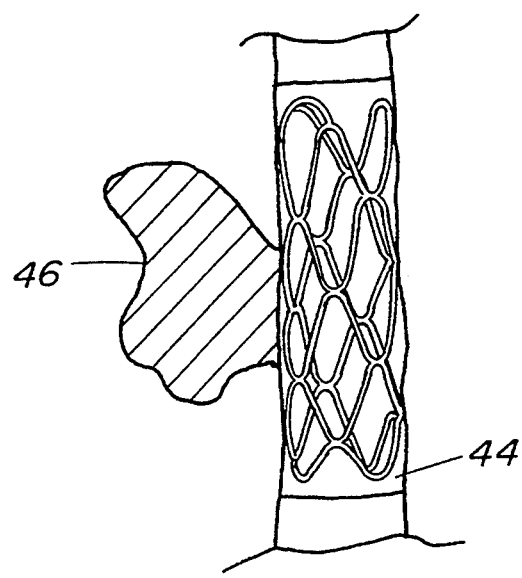
FIG. 12 shows the stent of FIG. 5 being used with a graft to repair a pseudo-aneurysm in the common femoral artery.
Figure 13:
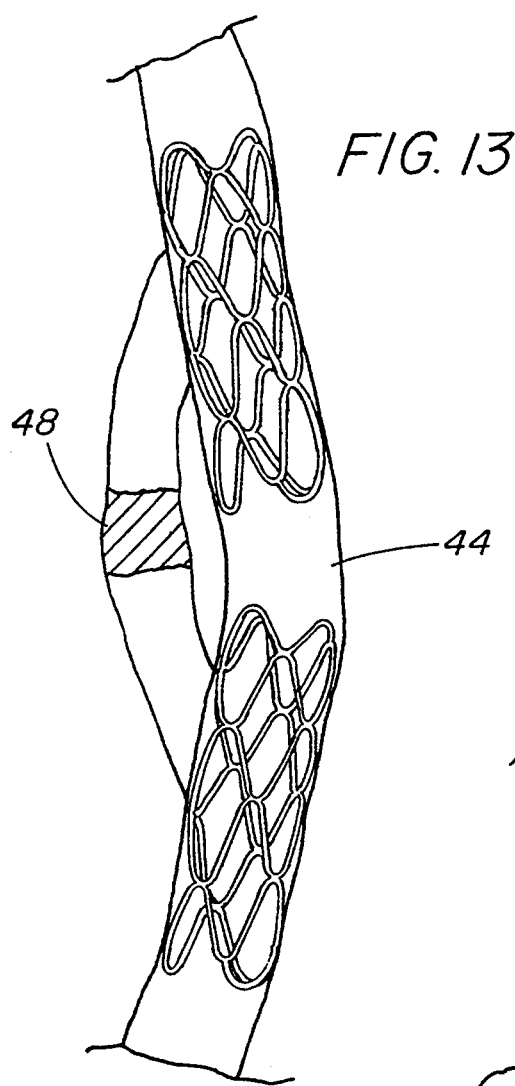
FIG. 13 shows two stents being used with a graft to bypass an occlusion in the femoral popliteal artery.
Figure 14:
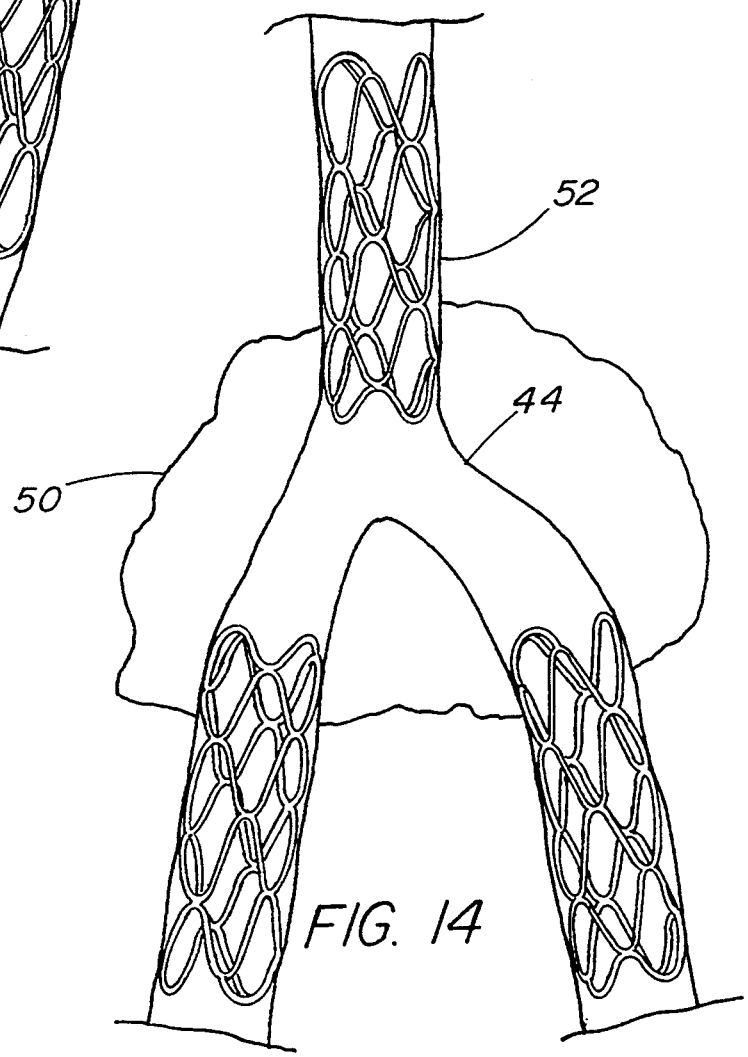
FIG. 14 shows three stents being used with graft to repair an aorta-iliac aneurysm.

FIG. 12 shows the stent, inside a graft, being used to repair a pseudo-aneurysm in a common femoral artery. The stent 8 is placed inside graft 44 which blocks off pseudo-aneurysm 46. Although the stent is shown to be completely inside graft 44, it may also extend outside the edges of the graft in order to provide additional support for the incisions at the end of the graft. FIG. 13 shows two stents being used at each end of graft 44 to bypass an occlusion 48 in, for example, the femoral-popliteal artery. FIG. 14 illustrates how three stents can be used with a branched graft to repair an aorto-iliac aneurysm 50.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A vascular stent, comprising:

a continuous wire forming a substantially tubular body with a plurality of cells staggered around a circumference of the tubular body, the tubular body being longitudinally flexible and having an expanded state, an unexpanded state, and a wall thickness that is not substantially greater than said wire, each of said cells having a plurality of sides formed by said continuous wire and shared with an other of said cells, adjacent sides in individual ones of said cells being joined by a bend in said continuous wire, selected of said cells each making non-overlapping and abutting contact with an other of said cells;

said sides of said cells extending substantially parallel to a longitudinal axis of the tubular body when the tubular body is in said unexpanded state; and said sides of said cells extending oblique to said longitudinal axis of the tubular body when the tubular body is in said expanded state, whereby said tubular body when positioned in a tortuous vessel bends along said longitudinal axis and conforms to the shape of the tortuous vessel an axial length of the tubular body being substantially equivalent in said unexpanded and said expanded state.

2. A vascular stent according to claim 1, wherein at least one of said cells is bonded to an adjacent cell at a position between two adjacent sides of each of said cells.

3. A vascular stent according to claim 1, wherein said cells have an oblong shape with a long axis of the oblong shape extending substantially parallel to the longitudinal axis of the tubular body.

4. A vascular stent according to claim 3, wherein said cells have four sides.

5. A vascular stent according to claim 4, wherein said four sides form a rhombic shape when said body is expanded.

6. A vascular stent according to claim 1, wherein said wire includes tantalum.

7. A vascular stent according to claim 1, wherein said wire is plastically deformed in said expanded state so that the tubular body retains in its shape in the expanded state.

8. A vascular stent according to claim 1, wherein said tubular body is arranged on a catheter.

9. A vascular stent, comprising:
a continuous wire forming a substantially tubular body with a longitudinal axis, said body having an unexpanded state and an expanded state;
said wire being formed into a generally sinusoidal wave pattern around a circumference of said tubular body wherein each wave in said wave pattern has an ascending side and a descending side with a peak between said ascending side and said descending side, and a valley between said descending side and an ascending side of an adjacent wave, the ascending and the descending sides in each wave pattern being of unequal length; and
said ascending and descending sides of each wave being arranged substantially parallel to said longitudinal axis of said body when said body is in an unexpanded state.

10. A vascular stent according to claim 9 wherein each pair of ascending and descending sides in each wave is arranged to swing away from each other when said body expanded radially to its expanded state.

11. A vascular stent according to claim 9 wherein the peak of one wave is bonded to the valley of another wave.

12. A vascular stent according to claim 9, wherein an apex of each peak adjacent to one end of said tubular body is aligned with a circumference of said tubular body.

13. A vascular stent according to claim 12, wherein an apex of each valley adjacent to an opposite end of said tubular body is aligned with a circumference of said tubular body.

14. A vascular stent according to claim 9, wherein said tubular body is arranged on a catheter.

15. The method of implanting the vascular stent of claim 14, comprising the steps of:
inserting a tubular balloon through an interior of said tubular body;
positioning said balloon and said tubular body in a patient's vascular passage;
inflating said balloon to cause radial expansion of said tubular body, said expansion applying sufficient stress on said wire to cause plastic deformation of said wire, so that said tubular body resists collapse when expanded;
withdrawing said balloon from the patient, while leaving said stent in said expanded state in the patient's vascular passage.

16. A method of making the vascular stent of claim 9, comprising the steps of:
forming said continuous wire into said sinusoidal wave pattern wherein each successive wave in said wave pattern includes an ascending side, a peak, a descending side, and a valley, and wherein the ascending and descending sides include substantially straight portions; and
wrapping said wire around a mandrel so that said straight portions are substantially aligned with a longitudinal axis of said mandrel.

17. The method of claim 16 further comprising the step of positioning the peak of one wave tangent to a valley of another wave on said mandrel and bonding the peak of said one wave to the valley of said other wave.

18. A stent comprising:
a continuous, malleable wire formed into a predetermined waveform pattern that includes a plurality of wire segments joined in a series by a plurality of bends;
said predetermined waveform pattern being formed about a longitudinal axis to define a hollow cylinder that includes a plurality of pairs of said bends in abutting contact and that has a wall thickness that is not substantially greater than said wire;
selected of said pairs of bends being bonded to one another and making a non-overlapping connection so that said hollow cylinder further includes a plurality of closed cells bounded on all sides by wire, sides of said closed cells being shared with one another; and
said hollow cylinder having a first diameter and at least a portion of said hollow cylinder being inelastically deformable from said first diameter to a second expanded diameter whereby an axial length of said hollow cylinder is substantially equivalent in an unexpanded and an expanded state.

19. The stent of claim 18 wherein selected of said closed cells are contiguous.

20. The stent of claim 18 wherein selected of said plurality of closed cells form a rhombic shape.

21. A method of making the stent of claim 18 comprising the steps of:
forming said continuous, malleable wire into said predetermined waveform pattern that includes said plurality of wire segments joined in said series by said plurality of bends;
forming said predetermined waveform pattern around said longitudinal axis to define a hollow cylinder that includes said plurality of pairs of said bends in said abutting contact and that has a wall thickness that is not substantially greater than said wire; and
bonding selected of said pairs together to form a non-overlapping connection so that said hollow cylinder further includes said plurality of closed cells bounded on all sides by said wire, sides of said closed cells being shared with one another.

* * * * *